United States Patent [19]

Seele et al.

[11] Patent Number: 5,098,917
[45] Date of Patent: Mar. 24, 1992

[54] SUBSTITUTED IMIDAZOLYLMETHYLOXIRANES AND SUBSTITUTED IMIDAZOLYPROPENES THEIR PREPARATION AND FUNGICIDES CONTAINING THEM

[75] Inventors: Rainer Seele, Fussgoenheim; Stefan Karbach, Neustadt; Norbert Goetz, Worms; Hubert Sauter, Mannheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 666,189

[22] Filed: Mar. 7, 1991

Related U.S. Application Data

[62] Division of Ser. No. 377,000, Jul. 7, 1989, Pat. No. 5,028,618.

[30] Foreign Application Priority Data

Jul. 28, 1988 [DE] Fed. Rep. of Germany ....... 3825586

[51] Int. Cl.$^5$ ................ A61K 31/415; C07D 401/06; C07D 233/64
[52] U.S. Cl. .................... 514/333; 514/341; 514/396; 514/397; 514/398; 514/399; 546/256; 546/278; 548/335; 548/336; 548/337; 548/338; 548/339; 548/341; 548/342; 548/343
[58] Field of Search ............ 546/256, 278; 548/335, 548/336, 337, 338, 339, 341, 342, 343; 514/333, 341, 396, 397, 398, 399

[56] References Cited

U.S. PATENT DOCUMENTS 4,464,381 8/1984 Janssen et al. .......... 424/269

Primary Examiner—Johann Richter
Attorney, Agent, or Firm—Oblon, Spivak, McClelland, Maier & Neustadt

[57] ABSTRACT

Substituted imidazolylmethyloxiranes and substituted imidazolylpropenes of the general formula I

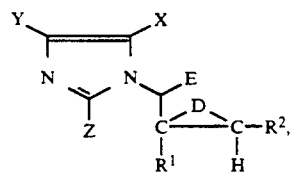

wherein
$R^1$ and $R^2$ are alkyl, cycloalkyl, cycloalkenyl, tetrahydropyranyl, norbornyl, pyridyl, naphthyl, biphenyl or phenyl,
D is oxygen or a single bond,
E is H, F, Cl or Br,
X, Y and Z are hydrogen, halogen, nitro, cyano, alkyl, haloalkyl, alkoxy, unsubstituted or substituted amino, unsubstituted or substituted mercapto, acyl, alkoxycarbonyl, hydroxyalkyl or substituted or unsubstituted phenyl, and acid addition salts and metal complexes thereof tolerated by plants,
processes for their manufacture, and fungicides containing them.

4 Claims, No Drawings

SUBSTITUTED IMIDAZOLYLMETHYLOXIRANES AND SUBSTITUTED IMIDAZOLYPROPENES THEIR PREPARATION AND FUNGICIDES CONTAINING THEM

This is a division of application Ser. No. 07/377,000, filed on July 7, 1989, now U.S. Pat. No. 5,028618.

The present invention relates to novel substituted imidazolylmethyloxiranes and substituted imidazolylpropenes, processes for their preparation and fungicides containing them, and methods for controlling fungi.

It is known that imidazolyloxiranes, for example cis-2-(imidazol-1-ylmethyl)-2-(4-fluorophenyl)-3-(2,6-difluorophenyl)-oxirane (DE-32 18 130) can be used as fungicides. However, the fungicidal actions are unsatisfactory.

We have found that substituted imidazolylmethyloxiranes and substituted imidazolylpropenes of the formula I

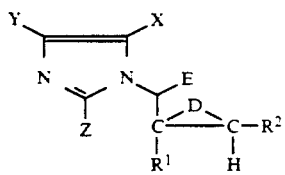

where $R^1$ and $R^2$ are identical or different and are each $C_1$–$C_8$-alkyl, $C_3$–$C_8$-cycloalkyl, $C_5$–$C_8$-cycloalkenyl, tetrahydropyranyl, norbornyl, pyridyl, naphthyl, biphenyl or phenyl, and these radicals may be monosubstituted to trisubstituted by halogen, nitro, phenoxy, amino, alkyl, alkoxy or haloalkyl, each of 1 to 4 carbon atoms, and D is O or a single bond, E is H, F, Cl or Br and X, Y and Z are identical or different and are each hydrogen, halogen, nitro, cyano, $C_1$–$C_3$-acyl, $C_1$–$C_3$-haloalkyl, $C_1$–$C_3$-alkoxy, amino which is unsubstituted or substituted by $C_1$–$C_3$-alkyl or $C_1$–$C_3$-acyl, unsubstituted or $C_1$–$C_3$-alkyl-substituted mercapto, $C_1$–$C_3$-acyl, $C_1$–$C_3$-alkoxycarbonyl, $C_1$–$C_3$-hydroxyalkyl or unsubstituted or substituted phenyl, and X, Y and Z cannot simultaneously be hydrogen, and their plant-tolerated acid addition salts and metal complexes have a better fungicidal action than known azole compounds.

The compounds of the formula I contain asymmetric carbon atoms and can therefore occur as enantiomers and diastereomers. In the case of the novel compounds, the mixtures of diastereomers can be separated in a conventional manner, for example on the basis of their different solubilities or by column chromatography, and can be isolated in pure form. The racemates of the novel compounds can be resolved by known methods, for example by salt formation with an optically active acid, separation of the diastereomeric salts and liberation of the enantiomers by means of a base. Both the pure diastereomers or enantiomers and the mixtures of these obtained in the synthesis can be used as fungicides.

$R^1$ and $R^2$ are each, for example, $C_1$–$C_8$-alkyl, in particular $C_1$–$C_4$-alkyl, such as methyl, ethyl, isopropyl, n-propyl, n-butyl, sec-butyl, tert-butyl, n-pentyl or neopentyl, 1-naphthyl, 2-naphthyl, p-biphenyl, phenyl, halophenyl, such as 2-chlorophenyl, 2-fluorophenyl, 2-bromophenyl, 3-chlorophenyl, 3-bromophenyl, 3-fluorophenyl, 4-fluorophenyl, 4-chlorophenyl, 4-bromophenyl, 2,4-dichlorophenyl, 2,3-dichlorophenyl, 2,5-dichlorophenyl, 2,6-dichlorophenyl, 2-chloro-6-fluorophenyl or 2-chloro-4-fluorophenyl, $C_1$–$C_4$-alkoxyphenyl, such as 2-methoxyphenyl, 3-methoxyphenyl, 4-methoxyphenyl, 2,4-dimethoxyphenyl or 3,4-dimethoxyphenyl, $C_1$–$C_4$-alkylphenyl, such as 4-ethylphenyl, 4-isopropylphenyl, 4-tert-butylphenyl or 4-tert-butoxyphenyl, 2-chloro-6-methylphenyl, 3-phenoxyphenyl, 4-phenoxyphenyl, 3-nitrophenyl, 4-nitrophenyl, 3-aminophenyl, 4-aminophenyl, 2-aminophenyl, 2-trifluoromethylphenyl, 3-trifluoromethylphenyl, 4-trifluoromethylphenyl, 3-pyridyl, tetrahydropyranyl, cyclopropyl, cyclopentyl, cyclohexyl, 2-cyclohexenyl, 3-cyclohexenyl or norbornyl.

X, Y and Z are each, for example, hydrogen, methyl, ethyl, propyl, isopropyl, trifluoromethyl, methoxy, ethoxy, methylamino, dimethylamino, acetylamino, diacetylamino, methylthio, acetyl, methoxyacetyl, phenyl, halophenyl, chlorophenyl or hydroxyethyl, and X, Y and Z cannot simultaneously be hydrogen, ie. one or more of the radicals X, Y and Z differ from hydrogen.

Acid addition salts are, for example, the hydrochlorides, bromides, sulfates, nitrates, phosphates, oxalates and dodecylbenzenesulfonates. The activity of the salts is attributable to the cation, so that the anion is generally unimportant. The novel active ingredients salts are prepared by reacting an imidazolylmethyloxirane (I) with an acid.

Metal complexes of the active ingredients I or their salts can be formed, for example, with copper, zinc, tin, manganese, iron, cobalt or nickel, by reacting the imidazolylmethyloxirane with a corresponding metal salt, for example with copper sulfate, zinc chloride, tin chloride or manganese sulfate.

The compounds of the formula I in which D is O and E is H can be prepared, for example by
a) reacting a compound of the formula II

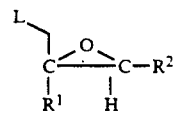

where $R^1$ and $R^2$ have the abovementioned meanings and L is a leaving group which can be substituted by a nucleophile (eg. halogen or OH), with a compound of the formula III

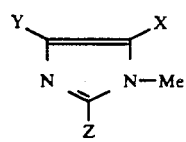

where Me is hydrogen, a metal atom (eg. Na or K) or trimethylsilyl and X, Y and Z have the abovementioned meanings, or
b) converting a compound of the formula IV

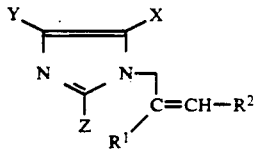

where $R^1$, $R^2$, X, Y and Z have the abovementioned meanings, into the epoxide.

If Me is hydrogen, reaction a) is carried out, for example, in the presence or absence of a base and in the presence or absence of a solvent or diluent, with or without the addition of a reaction accelerator, at from 10° to 120° C. The preferred solvents and diluents include ketones, such as acetone, methyl ethyl ketone and cyclohexanone, nitriles, such as acetonitrile and propionitrile, alcohols, such as methanol, ethanol, isopropanol, n-butanol and glycol, esters, such as ethyl acetate, methyl acetate and butyl acetate, ethers, such as tetrahydrofuran, diethyl ether, dimethoxyethane, dioxane and diisopropyl ether, amides, such as dimethylformamide, dimethylacetamide and N-methylpyrrolidone, and dimethyl sulfoxide, sulfolane and mixtures of these.

Suitable bases, which may also be used as acid acceptors in the reaction are, for example, alkali metal hydroxides, such as lithium hydroxide, sodium hydroxide or potassium hydroxide, alkali metal carbonates, such as sodium carbonate, potassium carbonate or cesium carbonate, or sodium bicarbonate, potassium bicarbonate, cesium bicarbonate, pyridine or 4-dimethylaminopyridine. However, other conventional bases may also be used.

Preferred reaction accelerators are metal halides, such as sodium iodide or potassium iodide, quaternary ammonium salts, such as tetrabutylammonium chloride, bromide, iodide or bisulfate, benzyltriethylammonium chloride or bromide, and crown ethers, such as 12-crown-4, 15-crown-5, 18-crown-6, dibenzo-18-crown-6 or dicyclohexano-18-crown-6.

The reaction is generally carried out, at, for example, from 20° to 150° C., under atmospheric or super atmospheric pressure, continuously or batchwise.

If Me is a metal atom, reaction a) is carried out, for example, in the presence or absence of a solvent or diluent and with or without the addition of a strong inorganic or organic base, at from $-10°$ to 120° C. The preferred solvents and diluents include amides, such as dimethylformamide, diethylformamide, dimethylacetamide, diethylacetamide, N-methylpyrrolidone, hexamethylphosphorotriamide, sulfoxides, such as dimethyl sulfoxide, and finally sulfolane.

Suitable bases, which may also be used as acid acceptors in the reaction, are, for example, alkali metal hydrides, such as lithium hydride, sodium hydride and potassium hydride, alkali metal amides, such as sodium amide and potassium amide, as well as sodium tert-butoxide, potassium tert-butoxide, triphenylmethyllithium, triphenylmethylsodium, triphenylmethylpotassium, naphthalenelithium, naphthalenesodium and naphthalenepotassium.

Examples of suitable diluents for reaction b) are polar organic solvents, such as nitriles, eg. acetonitrile, sulfoxides, eg. dimethyl sulfoxide, formamides, eg. dimethylformamide, ketones, eg. acetone, ethers, eg. diethyl ether or tetrahydrofuram, and in particular chlorohydrocarbons, eg. methylene chloride and chloroform.

The reaction is carried out in general at, for example, from 0° to 100° C., preferably from 20° to 80° C. In the presence of a solvent, it is advantageously carried out at the boiling point of the particular solvent.

The novel starting compounds II are obtained, for example, by epoxidation of the corresponding olefins V

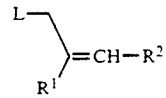

(cf. G. Dittus in Houben-Weyl-Müller, Methoden der Organischen Chemie, Georg Thieme Verlag, Stuttgart, 1965, Vol. VI, 3, page 385 et seq.).

The compound V is prepared by halogenating or oxidizing olefins of the formula IX

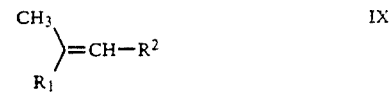

by know methods in the allyl position.

Suitable halogenating reagents are N-chloro- and N-bromosuccinimide in halohydrocarbons, such as carbon tetrachloride, trichloroethane or methylene chloride, temperatures of from 20° to 100° C. being employed. For the allyl oxidation, peresters, such as tert-butyl perbenzoate or tert-butyl peracetate, are used in the presence of a heavy metal salt, eg. copper(I) chloride or copper(I) bromide. The reaction is carried out in an inert solvent at from 10° to 100° C.

The allyl halides or alcohols V thus obtained are then converted into the corresponding epoxides II (L=halogen or OH). For this purpose, the olefins V are oxidized with a peroxycarboxylic acid, such as perbenzoic acid, 3-chloroperbenzoic acid, 4-nitroperbenzoic acid, monoperphthalic acid, peracetic acid, perpropionic acid, permaleic acid, monopersuccinic acid, perpelargonic acid or trifluoroperacetic acid, in an inert solvent, preferably a chlorohydrocarbon, eg. methylene chloride, chloroform, carbon tetrachloride or dichloroethane, or, if required, in acetic acid, ethyl acetate, acetone or dimethylformamide, in the presence or absence of a buffer, such as sodium acetate, sodium carbonate, disodium hydrogen phosphate or Triton B. The reaction is carried out at from 10° to 100° C. and, if required, is catalyzed with, for example, iodine, sodium tungstate or light. Alkaline solutions of hydrogen peroxide (about 30% strength) in methanol, ethanol, acetone or acetonitrile, at from 25° to 30° C., and alkyl hydroperoxides, eg. tert-butyl hydroperoxide, with the addition of a catalyst, eg. sodium tungstate, pertungstic acid, molybdenum hexacarbonyl or vanadyl acetylacetonate, are also suitable for the oxidation. Some of the state oxidizing agents can be produced in situ.

While the resulting epoxyhalides II (L=halogen) can be reacted immediately by process a), the corresponding epoxyalcohols II (L=OH) are converted into, for example, reactive esters, which are then reacted with the compounds III by process a).

The reactive esters which can be reacted with III are prepared by generally known methods.(Houben-Weyl-Müller, Methoden der organischen Chemie, Georg Thieme Verlag, Stuttgart, 1955, Volume 9, pages 388, 663 and 671). Examples of such esters are methanesulfonates, trifluoromethanesulfonates, 2,2,2-trifluoroethanesulfonates, nonafluorobutanesulfonates, 4-methylbenzenesulfonates, 4-bromobenzenesulfonates, 4-nitrobenzenesulfonates and benzenesulfonates.

The compounds V can be prepared by generally known processes of olefin synthesis (Houben-Weyl- Müller, Methoden der organischen Chemie, Georg Thieme Verlag, Stuttgart, 1972, Vol. V, 1b).

The compounds of the formula IV

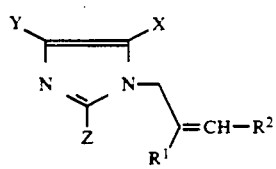

are obtained, for example, by
a) reacting a compound of the formula V

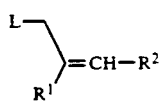

where $R^1$ and $R^2$ have the abovementioned meanings and L is a leaving group which can be substituted by a nucleophile, with a compound of the formula III

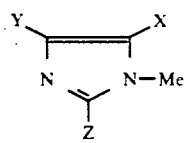

where Me is hydrogen, a metal atom or trimethylsilyl and X, Y and Z have the above mentioned meanings, or reacting a compound of the formula VI

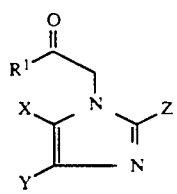

where $R^1$, X, Y and Z have the abovementioned meanings, with a compound of the formula VII

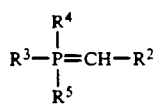

where $R^2$ has the same meanings as in formula I and $R^3$, $R^4$ and $R^5$ may be identical or different and are each phenyl, p-carboxyphenyl, p-dimethylaminophenyl, dimethylamino, piperidino, morpholino, alkyl of 1 to 3 carbon atoms or cyclohexyl.

The compounds of the formula I in which E is F, Cl or Br can be prepared, for example, by reacting a compound of the formula VIII

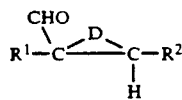

where $R^1$, $R^2$ and D have the state meanings, with a compound of the formula III

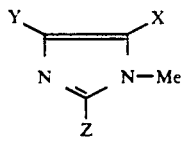

where X, Y, Z and Me have the abovementioned meanings, in the presence of a thionyl halide.

The reaction is carried out, for example, in the presence or absence of a solvent or diluent at from $-30°$ to $80°$ C. The preferred solvents and diluents include nitriles, such as acetonitrile or, propionitrile, ethers, such as tetrahydrofuran, diethyl ether, dimethoxyethane, dioxane or diisopropyl ether, and in particular hydrocarbons and chlorohydrocarbons, such as pentane, hexane, toluene, methylene chloride, chloroform, carbon tetrachloride or dichloroethane, or mixtures of these.

The novel starting compounds VIII in which D is O are obtained, for example, by epoxidation of the corresponding olefins X

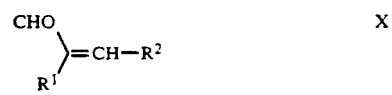

(cf. G. Dittus in Houben-Weyl-Müller, Methoden der Organischen Chemie, Georg Thieme Verlag, Stuttgart, 1965, Vol. VI, 3, page 38 et seq.).

The compounds X can be prepared by generally known methods of aldehyde synthesis (Houben-Weyl-Müller, Methoden der Organischen Chemie, Georg Thieme Verlag, Stuttgart, 1983, Vol. E3).

The Examples which follow illustrate the preparation of the active ingredients.

I. PREPARATION OF THE STARTING MATERIALS

EXAMPLE A 8.4 g of sodium hydroxide in 40 ml of water are added to a solution of 85.5 g of 2-trifluoromethylbenzaldehyde in 300 ml of methanol. The reaction mixture is cooled to 10° C. and 69 g of 4-fluorophenylacetaldehyde are rapidly added dropwise, the temperature of the solution not exceeding 30° C. After stirring has been carried out for two hours at room temperature, 300 ml of water are added to the colorless reaction solution, and the resulting emulsion is extracted by shaking with methyl tert-butyl ether. The organic phase is separated off, dried over sodium sulfate and evaporated down under reduced pressure. In the subsequent distillation of the remaining residue, 96 g (65%) of E-2-(4-fluorophenyl)-3-(2-trifluoromethylphenyl)-propenal are obtained at 116° C./0.3 mbar.

EXAMPLE B 96 g of E-2-(-4-fluorophenyl)-3-(2-trifluoromethylphenyl)-propenal are dissolved in 300 ml of methanol and 2.3 ml of concentrated sodium hydroxide solution are added. The reaction solution is stirred at 0° C. while 27.7 g of about 50% strength hydrogen peroxide are slowly added dropwise, the internal temperature not exceeding 30° C. After the end of the addition, stirring is continued for 6 hours at room temperature (20° C.), after which 5 g of sodium borohydride, which has been dissolved in a little 10% strength sodium hydroxide solution, are added. After the reaction mixture has been stirred for 18 hours at room temperature, 100 ml of water are added to the solution and the resulting emulsion is extracted by shaking with methylene chloride. The organic phase isolated is then dried over sodium sulfate and evaporated down. 90 g (89%) of cis-2-hydroxymethyl-2-(4-fluorophenyl)-3-(2-trifluoromethylphenyl)-oxirane are obtained.

EXAMPLE C 61 g of 4-methlbenzenesulfonyl chloride are added to a solution of 90 g of cis-2-hydroxymethyl-2-(4-fluorophenyl)-3-(2-trifluoromethylphenyl)-oxirane in 300 ml of methylene chloride and 58 g of triethylamine at room temperature. After 24 hours, the reaction mixture is washed with aqueous sodium bicarbonate solution and water and evaporated down under reduced pressure. The residue gives 128.4 g (95%) of cis-2-(4-methylphenylsulfonyloxymethyl)-2-(4-fluorophenyl)-3-(2-trifluoromethylphenyl)-oxirane, which is then further processed with triazole.

EXAMPLE D 7.3 g of sodium borohydride, which has been dissolved in a little 10% strength sodium hydroxide solution are added to a solution of 150 g of E-2-(4-fluorophenyl)-3-(2-chlorophenyl)-propenal (prepared as described in Example A) in 600 ml of isopropanol at 0° C. After the reaction mixture has been stirred for two hours at room temperature, 300 ml of water are added to the solution and the resulting emulsion is extracted by shaking with methylene chloride. The organic phase isolated is then dried over sodium sulfate and evaporated down. 150.7 g (100%) of E-2-(4-fluorophenyl)-3-(2-chlorophenyl)-prop-2-enol are obtained.

EXAMPLE E 103.1 g of E-2-(4-fluoropehnyl)-3-(2-chlorophenyl)-prop-2-enol are dissolved in 700 ml of methyl tert-butyl ether, and 2 ml of pyridine are added. The reaction solution is stirred under a nitrogen atmosphere at 0° C., while 27.2 g of phosphorus tribromide are added in the course of 90 minutes. After the end of the addition, the mixture is refluxed for two hours and then poured onto 500 ml of water and extracted several times with methyl tert-butyl ether. The organic phase is washed with sodium bicarbonate solution and water and dried over sodium sulfate, and the solvent is evaporated down under reduced pressure. 77.2 g (61%) of E-1-bromo-2-(4-fluorophenyl)-3-(2-chlorophenyl)-prop-2-ene of melting point 68° C. are obtained from ethanol.

EXAMPLE F 77.2 g of E-1-bromo-2-(4-fluorophenyl)-3-(2-chlorophenyl)-prop-2-ene are heated at 180° C. for one hour. The reaction mixture is cooled to room temperature and 200 ml of ethanol are added. Thereafter, 10 g of active carbon are added and the mixture is heated to 50° C. and filtered while hot. 26.9 g (35%) of Z-1-bromo-2-(4-fluorophenyl)-3-(2-chlorophenyl)-prop-2-ene of melting point 73°-75° C. are obtained from ethanol.

EXAMPLE G 78.2 g of E-2-(4-fluorophenyl)-3-(2-chlorophenyl)-propenal are dissolved in 300 ml of methanol, and 1 ml of concentrated sodium hydroxide solution is added. The reaction solution is stirred at 0° C. while 20.5 g of about 50% strength hydrogen peroxide are slowing added dropwise, the internal temperature not exceeding 30° C. After the end of the addition, the mixture is stirred for six hours at room temperature, after which 100 ml of water are added and the resulting emulsion is extracted by shaking with methyl tert-butyl ether. The organic phase isolated is then dried over sodium sulfate and evaporated down. 52.5 g (63%) of cis-2-formyl-2-(4-fluorophenyl)-3-(2-chlorophenyl)-oxirane are obtained.

II. PREPARATION OF THE END PRODUCTS

EXAMPLE 1

55 g of 4,5-dichloroimidazole and 9.5 g of sodium hydride (80% strength dispersion in mineral oil) are suspended in 300 ml of N,N-dimethylformamide and a solution of 128.4 g of cis-2-(4-methylphenylsulfonyloxymethyl)-2-(4-fluorophenyl)-3-(2-trifluoromethylphenyl) -oxirane in 200 ml of N,N-dimethylformamide is added at room temperature. After eight hours, the reaction solution is poured onto water and extracted with methyl tert-butyl ether. The organic phase is washed with water and dried over sodium sulfate and the solvent is evaporated down under reduce pressure. 86.4 g (76%) of cis-2-(4,5-dichloroimidazol-1-ylmethyl)-2-(4-fluorophenyl)-3-( 2-trifluoromethylphenyl)-oxirane of melting point 158° C. (compound) No. 1) are obtained from methyl tert-butyl ether/n-hexane.

The compounds listed in Table 1 can be prepared similarly to Example 1.

EXAMPLE 2

15 g of 5-nitroimidazole and 31 g of potassium carbonate are added to a solution of 7.5 g of Z-1-bromo-2-(4-fluorophenyl)-3-(2-chlorophenyl)-prop-2-ene in 40 ml of dimethylformamide. After the reaction mixture has been stirred for 24 hours at room temperature, 50 ml of water are added and the mixture is extracted several times with methyl tert-butyl ether; the organic phase is washed with water, dried over sodium sulfate and evaporated down under reduced pressure. 6.7 g (81%) of Z-1-(5-nitroimidazol-1-yl)-2-(4-fluorophenyl)-3-( 2-chlorophenyl)-prop-2-ene of melting point 161°-165° C. (compound No. 1a) are obtained from methyl tert-butyl ether/n-hexane.

The compounds listed in Table 2 can be prepared similarly to Example 2.

EXAMPLE 3

13.1 g of thionyl chloride are added to a solution of 27.7 g of methyl 4-imidazolecarboxylate in 150 ml of methylene chloride at 0° C. After the end of the addition, the mixture is stirred for 30 minutes at room temperature and 18.5 g of cis-2-formyl-2-(4-fluorophenyl)-3-(2-chlorophenyl)-oxirane are then added. After the reaction mixture has been stirred for 12-15 hours at room temperature, 100 ml of water are added to the solution and the organic phase is separated off. The remaining aqueous phase is extracted twice by shaking with methylene chloride and the collected organic phases are washed twice with saturated sodium bicarbonate solution. The organic phase isolated is then dried over sodium sulfate and evaporated down. 14.3 g (53%) of cis-2-[1-(4-methoxycarbonylimidazol-1-yl)-1-chloromethyl]-2-(4-fluorophenyl)-3-(2-chlorophenyl)-oxirane of melting point 199°-203° C. (compound No. 25) are obtained from methyl tert-butyl ether.

The compounds listed is Table 1 can be prepared similarly to Example 3.

EXAMPLE 4

13.1 g of thionyl chloride are added to a solution of 30.1 g of 4,5-dichloroimidazole in 150 ml of methylene chloride at 0° C. After the end of the addition, the mixture is stirred for 30 minutes at room temperature and 17.4 g of E-2-(4-fluorophenyl)-3-(2-chlorophenyl)-propenal are then added. After the reaction mixture has been stirred for 12-15 hours at room temperature, 100 ml of water are added to the solution and the organic phase is separated off. The remaining aqueous phase is extracted twice by shaking with methylene chloride and the collected organic phases are washed twice with saturated sodium bicarbonate solution. The organic phase isolated is then dried over sodium sulfate and evaporated down, and the residue is purified by chromatography over silica gel using 9:1 ethyl acetate n-hexane. 24.8 (89%) of E-1-chloro-1-(4,5-dichloroimidazol-1-yl)-2-(4-fluorophenyl)-3-(2-chlorophenyl)-prop-2-ene (compound No. 8a) are obtained.

The compounds listed in Table 2 can be prepared similarly to Example 4.

TABLE 1

I

| Ex. | $R^1$ | $R^2$ | E | X | Y | Z | m.p./IR | Isomer |
|---|---|---|---|---|---|---|---|---|
| 1 | 4-F—$C_6H_4$ | 2-$CF_3$—$C_6H_4$ | H | Cl | Cl | H | 158° C. | cis |
| 2 | 4-F—$C_6H_4$ | 2-$CF_3$—$C_6H_4$ | H | H | $CO_2CH_3$ | H | 1699, 1514, 1315 1222, 1123, 771, $cm^{-1}$ | cis |
| 3 | 4-F—$C_6H_4$ | 2-$CF_3$—$C_6H_4$ | H | Cl | $CH_3$ | H | 164-167° C. | cis |
| 4 | 4-F—$C_6H_4$ | 2-$CF_3$—$C_6H_4$ | H | H | H | $CH_3$ | | |
| 5 | 4-F—$C_6H_4$ | 2-$CF_3$—$C_6H_4$ | H | H | CN | H | | |
| 6 | 4-F—$C_6H_4$ | 2-$CF_3$—$C_6H_4$ | H | $NO_2$ | H | H | | |
| 7 | 4-F—$C_6H_4$ | 2-$CF_3$—$C_6H_4$ | H | H | $CH_3$ | H | | |
| 8 | 4-F—$C_6H_4$ | 2-$CF_3$—$C_6H_4$ | Cl | Cl | Cl | H | | |
| 9 | 4-F—$C_6H_4$ | 2-$CF_3$—$C_6H_4$ | Cl | H | $CO_2CH_3$ | H | | |
| 10 | 4-F—$C_6H_4$ | 2-$CF_3$—$C_6H_4$ | Cl | Cl | $CH_3$ | H | | |
| 11 | 4-F—$C_6H_4$ | 2-$CF_3$—$C_6H_4$ | Cl | H | H | $CH_3$ | | |
| 12 | 4-F—$C_6H_4$ | 2-$CF_3$—$C_6H_4$ | Cl | H | CN | H | | |
| 13 | 4-F—$C_6H_4$ | 2-$CF_3$—$C_6H_4$ | Cl | $NO_2$ | H | H | | |
| 14 | 4-F—$C_6H_4$ | 2-$CF_3$—$C_6H_4$ | Br | Cl | Cl | H | | |
| 15 | 4-F—$C_6H_4$ | 2-$CF_3$—$C_6H_4$ | Br | H | $CO_2CH_3$ | H | | |
| 16 | 4-F—$C_6H_4$ | 2-$CF_3$—$C_6H_4$ | Br | H | $CH_3$ | H | | |
| 17 | 4-F—$C_6H_4$ | 2-Cl—$C_6H_4$ | H | Cl | Cl | H | 108-115° C. | cis |
| 18 | 4-F—$C_6H_4$ | 2-Cl—$C_6H_4$ | H | H | $CO_2CH_3$ | H | resin | cis |
| 19 | 4-F—$C_6H_4$ | 2-Cl—$C_6H_4$ | H | Cl | $CH_3$ | H | 112-113° C. | cis |
| 20 | 4-F—$C_6H_4$ | 2-Cl—$C_6H_4$ | H | H | H | $CH_3$ | 100-103° C. | cis |
| 21 | 4-F—$C_6H_4$ | 2-Cl—$C_6H_4$ | H | H | CN | H | 128-131° C. | cis |
| 22 | 4-F—$C_6H_4$ | 2-Cl—$C_6H_4$ | H | H | $NO_2$ | H | 206-208° C. | cis |
| 23 | 4-F—$C_6H_4$ | 2-Cl—$C_6H_4$ | H | H | $CH_3$ | H | resin | cis |
| 24 | 4-F—$C_6H_4$ | 2-Cl—$C_6H_4$ | Cl | Cl | Cl | H | 156-158° C. | cis |
| 25 | 4-F—$C_6H_4$ | 2-Cl—$C_6H_4$ | Cl | H | $CO_2CH_3$ | H | 199-203° C. | cis |
| 26 | 4-F—$C_6H_4$ | 2-Cl—$C_6H_4$ | Cl | Cl | $CH_3$ | H | 146-156° C. | D1:D2 = 1:1 |
| 27 | 4-F—$C_6H_4$ | 2-Cl—$C_6H_4$ | Cl | H | H | $CH_3$ | | |
| 28 | 4-F—$C_6H_4$ | 2-Cl—$C_6H_4$ | Cl | H | CN | H | 50-60° C. | D1:D2 = 2:1 |
| 29 | 4-F—$C_6H_4$ | 2-Cl—$C_6H_4$ | Cl | $NO_2$ | H | H | | |
| 30 | 4-F—$C_6H_4$ | 2-Cl—$C_6H_4$ | Cl | H | $CH_3$ | H | | |
| 31 | 4-F—$C_6H_4$ | 2-Cl—$C_6H_4$ | Br | Cl | Cl | H | 115-122° C. | D1:D2 = 4:1 |
| 32 | 4-F—$C_6H_4$ | 2-Cl—$C_6H_4$ | Br | H | $CO_2CH_3$ | H | 162° C. | cis |
| 33 | 4-F—$C_6H_4$ | 2-Cl—$C_6H_4$ | Br | Cl | $CH_3$ | H | | |
| 34 | 4-F—$C_6H_4$ | 2-Cl—$C_6H_4$ | Br | H | H | $CH_3$ | | |
| 35 | 4-F—$C_6H_4$ | 2-Cl—$C_6H_4$ | Br | H | CN | H | | |
| 36 | 4-F—$C_6H_4$ | 2-Cl—$C_6H_4$ | Br | $NO_2$ | H | H | | |
| 37 | 4-F—$C_6H_4$ | 4-Cl—$C_6H_4$ | H | Cl | Cl | H | 146-148° C. | cis |
| 38 | 4-F—$C_6H_4$ | 4-Cl—$C_6H_4$ | H | H | $CO_2CH_3$ | H | 138-141° C. | cis |
| 39 | 4-F—$C_6H_4$ | 4-Cl—$C_6H_4$ | H | Cl | $CH_3$ | H | 124-126° C. | cis |
| 40 | 4-F—$C_6H_4$ | 4-Cl—$C_6H_4$ | H | H | H | $CH_3$ | | |
| 41 | 4-F—$C_6H_4$ | 4-Cl—$C_6H_4$ | H | H | CN | H | | |
| 42 | 4-F—$C_6H_4$ | 4-Cl—$C_6H_4$ | H | $NO_2$ | H | H | | |
| 43 | 4-F—$C_6H_4$ | 4-Cl—$C_6H_4$ | H | H | $COCH_3$ | H | 127-130° C. | cis |
| 44 | 4-F—$C_6H_4$ | 4-Cl—$C_6H_4$ | Cl | Cl | Cl | H | | |
| 45 | 4-F—$C_6H_4$ | 4-Cl—$C_6H_4$ | Cl | H | $CO_2CH_3$ | H | | |
| 46 | 4-F—$C_6H_4$ | 4-Cl—$C_6H_4$ | Cl | Cl | $CH_3$ | H | | |
| 47 | 4-F—$C_6H_4$ | 4-Cl—$C_6H_4$ | Cl | H | H | $CH_3$ | | |
| 48 | 4-F—$C_6H_4$ | 4-Cl—$C_6H_4$ | Cl | H | CN | H | | |
| 49 | 4-F—$C_6H_4$ | 4-Cl—$C_6H_4$ | Cl | $NO_2$ | H | H | | |
| 50 | 4-F—$C_6H_4$ | 4-Cl—$C_6H_4$ | Br | Cl | Cl | H | | |
| 51 | 4-F—$C_6H_4$ | 4-Cl—$C_6H_4$ | Br | H | $CO_2CH_3$ | H | | |
| 52 | 4-F—$C_6H_4$ | 4-Cl—$C_6H_4$ | Br | Cl | $CH_3$ | H | | |
| 53 | 4-F—$C_6H_4$ | 4-Cl—$C_6H_4$ | Br | H | H | $CH_3$ | | |
| 54 | 4-F—$C_6H_4$ | 4-Cl—$C_6H_4$ | Br | H | CN | H | | |
| 55 | 4-F—$C_6H_4$ | 4-Cl—$C_6H_4$ | Br | $NO_2$ | H | H | | |
| 56 | 4-F—$C_6H_4$ | 4-Cl—$C_6H_4$ | Br | H | $CH_3$ | H | | |

TABLE 1-continued

I

| Ex. | R¹ | R² | E | X | Y | Z | m.p./IR | Isomer |
|---|---|---|---|---|---|---|---|---|
| 57 | 4-F—C₆H₄ | 2-Cl-4-F—C₆H₃ | H | Cl | Cl | H | 105–110° C. | cis |
| 58 | 4-F—C₆H₄ | 2-Cl-4-F—C₆H₃ | H | H | CO₂CH₃ | H | resin | cis |
| 59 | 4-F—C₆H₄ | 2-Cl-4-F—C₆H₃ | H | Cl | CH₃ | H | 150° C. | cis |
| 60 | 4-F—C₆H₄ | 2-Cl-4-F—C₆H₃ | H | H | H | CH₃ | | |
| 61 | 4-F—C₆H₄ | 2-Cl-4-F—C₆H₃ | H | H | CN | H | | |
| 62 | 4-F—C₆H₄ | 2-Cl-4-F—C₆H₃ | H | NO₂ | H | H | | |
| 63 | 4-F—C₆H₄ | 2-Cl-4-F—C₆H₃ | H | H | CH₃ | H | | |
| 64 | 4-F—C₆H₄ | 2-Cl-4-F—C₆H₃ | Cl | Cl | Cl | H | 145–149° C. | D1:D2 = 2:1 |
| 65 | 4-F—C₆H₄ | 2-Cl-4-F—C₆H₃ | Cl | H | CO₂CH₃ | H | | |
| 66 | 4-F—C₆H₄ | 2-Cl-4-F—C₆H₃ | Cl | Cl | CH₃ | H | | |
| 67 | 4-F—C₆H₄ | 2-Cl-4-F—C₆H₃ | Cl | H | H | CH₃ | | |
| 68 | 4-F—C₆H₄ | 2-Cl-4-F—C₆H₃ | Cl | H | CN | H | | |
| 69 | 4-F—C₆H₄ | 2-Cl-4-F—C₆H₃ | Cl | NO₂ | H | H | | |
| 70 | 4-F—C₆H₄ | 2-Cl-4-F—C₆H₃ | Cl | H | CH₃ | H | | |
| 71 | 4-F—C₆H₄ | 2-Cl-4-F—C₆H₃ | Br | Cl | Cl | H | | |
| 72 | 4-F—C₆H₄ | 2-Cl-4-F—C₆H₃ | Br | H | CO₂CH₃ | H | | |
| 73 | 4-F—C₆H₄ | 2-Cl-4-F—C₆H₃ | Br | Cl | CH₃ | H | | |
| 74 | 4-F—C₆H₄ | 2-Cl-4-F—C₆H₃ | Br | H | H | CH₃ | | |
| 75 | 4-F—C₆H₄ | 2-Cl-4-F—C₆H₃ | Br | H | CN | H | | |
| 76 | 4-F—C₆H₄ | 2-Cl-4-F—C₆H₃ | Br | NO₂ | H | H | | |
| 77 | 4-F—C₆H₄ | 2-Cl-4-F—C₆H₃ | Br | H | CH₃ | H | | |
| 78 | 4-F—C₆H₄ | 2-F—C₆H₄ | H | Cl | Cl | H | | |
| 79 | 4-F—C₆H₄ | 2-F—C₆H₄ | H | H | CO₂CH₃ | H | | |
| 80 | 4-F—C₆H₄ | 2-F—C₆H₄ | H | Cl | CH₃ | H | | |
| 81 | 4-F—C₆H₄ | 2-F—C₆H₄ | Cl | Cl | Cl | H | | |
| 82 | 4-F—C₆H₄ | 2-F—C₆H₄ | Cl | H | CO₂CH₃ | H | | |
| 83 | 4-F—C₆H₄ | 2-F—C₆H₄ | Cl | Cl | CH₃ | H | | |
| 84 | 4-F—C₆H₄ | 2-F—C₆H₄ | Br | Cl | Cl | H | | |
| 85 | 4-F—C₆H₄ | 2-F—C₆H₄ | Br | H | CO₂CH₃ | H | | |
| 86 | 4-F—C₆H₄ | 2-F—C₆H₄ | Br | H | CH₃ | H | | |
| 87 | 4-F—C₆H₄ | 4-F—C₆H₄ | H | Cl | Cl | H | | |
| 88 | 4-F—C₆H₄ | 4-F—C₆H₄ | H | H | CO₂CH₃ | H | | |
| 89 | 4-F—C₆H₄ | 4-F—C₆H₄ | H | Cl | CH₃ | H | | |
| 90 | 4-F—C₆H₄ | 4-F—C₆H₄ | H | H | CH₃ | H | | |
| 91 | 4-F—C₆H₄ | 4-F—C₆H₄ | Cl | Cl | Cl | H | | |
| 92 | 4-F—C₆H₄ | 4-F—C₆H₄ | Cl | H | CO₂CH₃ | H | | |
| 93 | 4-F—C₆H₄ | 4-F—C₆H₄ | Cl | Cl | CH₃ | H | | |
| 94 | 4-F—C₆H₄ | 4-F—C₆H₄ | Cl | H | CH₃ | H | | |
| 95 | 4-F—C₆H₄ | 4-F—C₆H₄ | Br | Cl | Cl | H | | |
| 96 | 4-F—C₆H₄ | 4-F—C₆H₄ | Br | H | CO₂CH₃ | H | | |
| 97 | 4-F—C₆H₄ | 4-F—C₆H₄ | Br | Cl | CH₃ | H | | |
| 98 | 4-F—C₆H₄ | 4-F—C₆H₄ | Br | H | CH₃ | H | | |
| 99 | 4-F—C₆H₄ | 2,4-F₂—C₆H₃ | H | Cl | Cl | H | resin | cis |
| 100 | 4-F—C₆H₄ | 2,4-F₂—C₆H₃ | H | H | CO₂CH₃ | H | 141–144° C. | cis |
| 101 | 4-F—C₆H₄ | 2,4-F₂—C₆H₃ | H | Cl | CH₃ | H | 144–147° C. | cis |
| 102 | 4-F—C₆H₄ | 2,4-F₂—C₆H₃ | H | H | COCH₃ | H | resin | cis |
| 103 | 4-F—C₆H₄ | 2,4-F₂—C₆H₃ | H | H | H | CH₃ | | |
| 104 | 4-F—C₆H₄ | 2,4-F₂—C₆H₃ | Cl | Cl | Cl | H | 1607, 1507, 1463, 1237, 964 cm$^{-1}$ | D₁:D₂ = 2:1 |
| 105 | 4-F—C₆H₄ | 2,4-F₂—C₆H₃ | Cl | H | CO₂CH₃ | H | | |
| 106 | 4-F—C₆H₄ | 2,4-F₂—C₆H₃ | Cl | Cl | CH₃ | H | | |
| 107 | 4-F—C₆H₄ | 2,4-F₂—C₆H₃ | Cl | H | CH₃ | H | | |
| 108 | 4-F—C₆H₄ | 2,4-F₂—C₆H₃ | Cl | H | H | CH₃ | | |
| 109 | 4-F—C₆H₄ | 2,4-F₂—C₆H₃ | Br | Cl | Cl | H | | |
| 110 | 4-F—C₆H₄ | 2,4-F₂—C₆H₃ | Br | H | CO₂CH₃ | H | | |
| 111 | 4-F—C₆H₄ | 2,4-F₂—C₆H₃ | Br | Cl | CH₃ | H | | |
| 112 | 4-F—C₆H₄ | 2,6-F₂—C₆H₃ | H | Cl | Cl | H | 131–132° C. | cis |
| 113 | 4-F—C₆H₄ | 2,6-F₂—C₆H₃ | H | H | CO₂CH₃ | H | resin | cis |
| 114 | 4-F—C₆H₄ | 2,6-F₂—C₆H₃ | H | Cl | CH₃ | H | 129–132° C. | cis |
| 115 | 4-F—C₆H₄ | 2,6-F₂—C₆H₃ | H | H | COCH₃ | H | resin | cis |
| 116 | 4-F—C₆H₄ | 2,6-F₂—C₆H₃ | Cl | H | CO₂CH₃ | H | | |
| 117 | 4-F—C₆H₄ | 2,6-F₂—C₆H₃ | Cl | Cl | CH₃ | H | | |
| 118 | 4-F—C₆H₄ | 2,6-F₂—C₆H₃ | Br | Cl | Cl | H | | |
| 119 | 4-F—C₆H₄ | 2,6-F₂—C₆H₃ | Br | H | CO₂CH₃ | H | | |
| 120 | 4-F—C₆H₄ | 2,6-F₂—C₆H₃ | Br | H | H | CH₃ | | |
| 121 | 4-F—C₆H₄ | 2,4-Cl₂—C₆H₃ | H | Cl | Cl | H | | |
| 122 | 4-F—C₆H₄ | 2,4-Cl₂—C₆H₃ | H | H | CO₂CH₃ | H | | |
| 123 | 4-F—C₆H₄ | 2,4-Cl₂—C₆H₃ | H | Cl | CH₃ | H | | |
| 124 | 4-F—C₆H₄ | 2,4-Cl₂—C₆H₃ | Cl | Cl | Cl | H | | |
| 125 | 4-F—C₆H₄ | 2,4-Cl₂—C₆H₃ | Cl | H | CO₂CH₃ | H | | |
| 126 | 4-F—C₆H₄ | 2,4-Cl₂—C₆H₃ | Cl | Cl | CH₃ | H | | |
| 127 | 4-F—C₆H₄ | 2,4-Cl₂—C₆H₃ | Br | Cl | Cl | H | | |

TABLE 1-continued $$\underset{Z}{\overset{Y}{\underset{}{\bigvee}}}\underset{}{\overset{X}{\underset{}{\bigvee}}}$$
(structure I with substituents R¹, R², E, X, Y, Z as shown)

| Ex. | R¹ | R² | E | X | Y | Z | m.p./IR | Isomer |
|---|---|---|---|---|---|---|---|---|
| 128 | 4-F—C₆H₄ | 2,4-Cl₂—C₆H₃ | Br | H | CO₂CH₃ | H | | |
| 129 | 4-F—C₆H₄ | 2,4-Cl₂—C₆H₃ | Br | Cl | CH₃ | H | | |
| 130 | 4-F—C₆H₄ | 2-OCH₃—C₆H₄ | H | Cl | Cl | H | | |
| 131 | 4-F—C₆H₄ | 2-OCH₃—C₆H₄ | H | H | CO₂CH₃ | H | 1731, 1514, 1494, 1245, 1223, 758 cm⁻¹ | cis |
| 132 | 4-F—C₆H₄ | 2-OCH₃—C₆H₄ | H | Cl | CH₃ | H | | |
| 133 | 4-F—C₆H₄ | 2-OCH₃—C₆H₄ | H | H | CH₃ | H | | |
| 134 | 4-F—C₆H₄ | 2-OCH₃—C₆H₄ | H | H | H | CH₃ | | |
| 135 | 4-F—C₆H₄ | 2-OCH₃—C₆H₄ | H | H | CN | H | | |
| 136 | 4-F—C₆H₄ | 2-OCH₃—C₆H₄ | H | NO₂ | H | H | | |
| 137 | 4-F—C₆H₄ | 2-OCH₃—C₆H₄ | Cl | Cl | Cl | H | 146-149° C. | cis |
| 138 | 4-F—C₆H₄ | 2-OCH₃—C₆H₄ | Cl | H | CO₂CH₃ | H | | |
| 139 | 4-F—C₆H₄ | 2-OCH₃—C₆H₄ | Cl | Cl | CH₃ | H | | |
| 140 | 4-F—C₆H₄ | 2-OCH₃—C₆H₄ | Cl | H | CH₃ | H | | |
| 141 | 4-F—C₆H₄ | 2-OCH₃—C₆H₄ | Cl | H | H | CH₃ | | |
| 142 | 4-F—C₆H₄ | 2-OCH₃—C₆H₄ | Cl | H | CN | H | | |
| 143 | 4-F—C₆H₄ | 2-OCH₃—C₆H₄ | Cl | NO₂ | H | H | | |
| 144 | 4-F—C₆H₄ | 2-OCH₃—C₆H₄ | Br | Cl | Cl | H | resin | D1:D2 = 3:1 |
| 145 | 4-F—C₆H₄ | 2-OCH₃—C₆H₄ | Br | H | CO₂CH₃ | H | | |
| 146 | 4-F—C₆H₄ | 2-OCH₃—C₆H₄ | Br | Cl | CH₃ | H | | |
| 147 | 4-F—C₆H₄ | 4-OCF₃—C₆H₄ | H | Cl | Cl | H | | |
| 148 | 4-F—C₆H₄ | 4-OCF₃—C₆H₄ | H | H | CO₂CH₃ | H | | |
| 149 | 4-F—C₆H₄ | 4-OCF₃—C₆H₄ | H | Cl | CH₃ | H | | |
| 150 | 4-F—C₆H₄ | 4-OCF₃—C₆H₄ | H | H | CH₃ | H | | |
| 151 | 4-F—C₆H₄ | 4-OCF₃—C₆H₄ | H | H | H | CH₃ | | |
| 152 | 4-F—C₆H₄ | 4-OCF₃—C₆H₄ | H | H | CN | H | | |
| 153 | 4-F—C₆H₄ | 4-OCF₃—C₆H₄ | Cl | Cl | Cl | H | | |
| 154 | 4-F—C₆H₄ | 4-OCF₃—C₆H₄ | Cl | H | CO₂CH₃ | H | | |
| 155 | 4-F—C₆H₄ | 4-OCF₃—C₆H₄ | Cl | Cl | CH₃ | H | | |
| 156 | 4-F—C₆H₄ | 4-OCF₃—C₆H₄ | Cl | H | CH₃ | H | | |
| 157 | 4-F—C₆H₄ | 4-OCF₃—C₆H₄ | Br | Cl | Cl | H | | |
| 158 | 4-F—C₆H₄ | 4-OCF₃—C₆H₄ | Br | H | CO₂CH₃ | H | | |
| 159 | 4-F—C₆H₄ | 4-OCF₃—C₆H₄ | Br | Cl | CH₃ | H | | |
| 160 | 4-F—C₆H₄ | 4-OCF₃—C₆H₄ | Br | H | CH₃ | H | | |
| 161 | 4-F—C₆H₄ | C₆H₅ | H | Cl | Cl | H | 125-128° C. | cis |
| 162 | 4-F—C₆H₄ | C₆H₅ | H | H | CO₂CH₃ | H | 116-120° C. | cis |
| 163 | 4-F—C₆H₄ | C₆H₅ | H | Cl | CH₃ | H | | |
| 164 | 4-F—C₆H₄ | C₆H₅ | H | H | CH₃ | H | | |
| 165 | 4-F—C₆H₄ | C₆H₅ | Cl | Cl | Cl | H | | |
| 166 | 4-F—C₆H₄ | C₆H₅ | Cl | H | CO₂CH₃ | H | | |
| 167 | 4-F—C₆H₄ | C₆H₅ | Cl | Cl | CH₃ | H | | |
| 168 | 4-F—C₆H₄ | C₆H₅ | Cl | H | CH₃ | H | | |
| 169 | 4-F—C₆H₄ | C₆H₅ | Br | Cl | Cl | H | | |
| 170 | 4-F—C₆H₄ | C₆H₅ | Br | H | CO₂CH₃ | H | | |
| 171 | 4-F—C₆H₄ | C₆H₅ | Br | Cl | CH₃ | H | | |
| 172 | 4-F—C₆H₄ | C₆H₅ | Br | H | CH₃ | H | | |
| 173 | 4-F—C₆H₄ | cyclohexyl | H | Cl | Cl | H | 2929, 1513, 1253, 837 cm⁻¹ | cis |
| 174 | 4-F—C₆H₄ | cyclohexyl | H | H | CO₂CH₃ | H | | |
| 175 | 4-F—C₆H₄ | cyclohexyl | H | Cl | CH₃ | H | | |
| 176 | 4-F—C₆H₄ | cyclohexyl | Cl | Cl | Cl | H | | |
| 177 | 4-F—C₆H₄ | cyclohexyl | Cl | H | CO₂CH₃ | H | | |
| 178 | 4-F—C₆H₄ | cyclohexyl | Cl | Cl | CH₃ | H | | |
| 179 | 4-F—C₆H₄ | cyclohexyl | Br | Cl | Cl | H | | |
| 180 | 4-F—C₆H₄ | cyclohexyl | Br | H | CO₂CH₃ | H | | |
| 181 | C₆H₅ | 2-Cl—C₆H₄ | H | Cl | Cl | H | 124-128° C. | cis |
| 182 | C₆H₅ | 2-Cl—C₆H₄ | H | H | CO₂CH₃ | H | resin | cis |
| 183 | C₆H₅ | 2-Cl—C₆H₄ | H | Cl | CH₃ | H | 142° C. | cis |
| 184 | C₆H₅ | 2-Cl—C₆H₄ | H | H | H | CH₃ | 89-90° C. | cis |
| 185 | C₆H₅ | 2-Cl—C₆H₄ | H | H | CN | H | 105-110° C. | cis |
| 186 | C₆H₅ | 2-Cl—C₆H₄ | H | NO₂ | H | H | 200° C. | cis |
| 187 | C₆H₅ | 2-Cl—C₆H₄ | H | H | CH₃ | H | 91-95° C. | cis/trans = 1.5:1 |
| 188 | C₆H₅ | 2-Cl—C₆H₄ | Cl | Cl | Cl | H | | |
| 189 | C₆H₅ | 2-Cl—C₆H₄ | Cl | H | CO₂CH₃ | H | | |
| 190 | C₆H₅ | 2-Cl—C₆H₄ | Cl | Cl | CH₃ | H | | |
| 191 | C₆H₅ | 2-Cl—C₆H₄ | Br | Cl | Cl | H | | |
| 192 | C₆H₅ | 2-Cl—C₆H₄ | Br | H | CO₂CH₃ | H | | |
| 193 | C₆H₅ | C₆H₅ | H | Cl | Cl | H | | |
| 194 | C₆H₅ | C₆H₅ | H | H | CO₂CH₃ | H | | |
| 195 | C₆H₅ | C₆H₅ | Cl | Cl | Cl | H | | |
| 196 | C₆H₅ | C₆H₅ | Cl | H | CO₂CH₃ | H | | |
| 197 | C₆H₅ | C₆H₅ | Br | Cl | Cl | H | | |

TABLE 1-continued

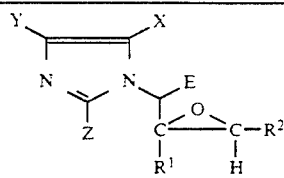

I

| Ex. | R¹ | R² | E | X | Y | Z | m.p./IR | Isomer |
|---|---|---|---|---|---|---|---|---|
| 198 | C₆H₅ | C₆H₅ | Br | H | CO₂CH₃ | H | | |
| 199 | C₆H₅ | 4-Cl—C₆H₄ | H | Cl | Cl | H | | |
| 200 | C₆H₅ | 4-Cl—C₆H₄ | Cl | Cl | Cl | H | | |
| 201 | C₆H₅ | 4-Cl—C₆H₄ | Br | Cl | Cl | H | | |
| 202 | C₆H₅ | 2,4-Cl₂—C₆H₃ | H | H | CO₂CH₃ | H | | |
| 203 | C₆H₅ | 2,4-Cl₂—C₆H₃ | Cl | Cl | Cl | H | | |
| 204 | C₆H₅ | 2,4-Cl₂—C₆H₃ | Br | Cl | CH₃ | H | | |
| 205 | C₆H₅ | 4-NO₂—C₆H₄ | H | Cl | Cl | H | | |
| 206 | C₆H₅ | 3-NO₂—C₆H₄ | H | H | CH₃ | H | | |
| 207 | C₆H₅ | cyclohexyl | H | CH₃ | Cl | H | | |
| 208 | 4-Cl—C₆H₄ | C₆H₅ | H | Cl | Cl | H | | |
| 209 | 4-Cl—C₆H₄ | C₆H₅ | Cl | Cl | Cl | H | | |
| 210 | 4-Cl—C₆H₄ | C₆H₅ | Br | H | CH₃ | H | | |
| 211 | 4-Cl—C₆H₄ | 4-Cl—C₆H₄ | H | Cl | Cl | H | | |
| 212 | 4-Cl—C₆H₄ | 4-Cl—C₆H₄ | Cl | Cl | Cl | H | | |
| 213 | 4-Cl—C₆H₄ | 4-Cl—C₆H₄ | Br | H | H | CH₃ | | |
| 214 | 4-Cl—C₆H₄ | 2,4-Cl₂—C₆H₃ | H | Cl | Cl | H | | |
| 215 | 4-Cl—C₆H₄ | 2,4-Cl₂—C₆H₃ | Cl | Cl | Cl | H | | |
| 216 | 4-Cl—C₆H₄ | 4-F—C₆H₄ | Cl | Cl | Cl | H | | |
| 217 | 4-Cl—C₆H₄ | 4-F—C₆H₄ | H | Cl | Cl | H | | |
| 218 | 4-Cl—C₆H₄ | 4-F—C₆H₄ | Br | H | CO₂CH₃ | H | | |
| 219 | 4-Cl—C₆H₄ | 2-F—C₆H₄ | H | Cl | Cl | H | | |
| 220 | 4-Cl—C₆H₄ | 2-F—C₆H₄ | Cl | Cl | Cl | H | | |
| 221 | 2-Cl—C₆H₄ | 2-Cl—C₆H₄ | H | Cl | Cl | H | | |
| 222 | 2-Cl—C₆H₄ | 2-Cl—C₆H₄ | Cl | Cl | Cl | H | | |
| 223 | 2-Cl—C₆H₄ | 2-Cl—C₆H₄ | Br | H | CH₃ | H | | |
| 224 | 2-Cl—C₆H₄ | 2-F—C₆H₄ | H | Cl | Cl | H | | |
| 225 | 2-Cl—C₆H₄ | 2-F—C₆H₄ | Cl | Cl | Cl | H | | |
| 226 | 2-Cl—C₆H₄ | 4-Cl—C₆H₄ | H | Cl | Cl | H | | |
| 227 | 2-Cl—C₆H₄ | 4-Cl—C₆H₄ | Cl | Cl | Cl | H | | |
| 228 | 2-F—C₆H₄ | 2-Cl—C₆H₄ | H | Cl | Cl | H | 87-94° C. | cis:trans = 3:1 |
| 229 | 2-F—C₆H₄ | 2-Cl—C₆H₄ | Cl | H | CH₃ | H | | |
| 230 | 2-F—C₆H₄ | 4-F—C₆H₄ | H | Cl | Cl | H | | |
| 231 | 2-F—C₆H₄ | 4-F—C₆H₄ | Cl | Cl | Cl | H | | |
| 232 | 2-F—C₆H₄ | 4-Cl—C₆H₄ | H | Cl | Cl | H | | |
| 233 | 2-F—C₆H₄ | 4-Cl—C₆H₄ | Cl | Cl | Cl | H | | |
| 234 | 2,4-Cl₂—C₆H₃ | 2-Cl—C₆H₄ | H | H | CH₃ | H | | |
| 235 | 2,4-Cl₂—C₆H₃ | 2-Cl—C₆H₄ | Cl | Cl | Cl | H | | |
| 236 | 2,4-Cl₂—C₆H₃ | 4-Cl—C₆H₄ | H | H | H | CH₃ | | |
| 237 | 2,4-Cl₂—C₆H₃ | 4-Cl—C₆H₄ | H | Cl | Cl | H | | |
| 238 | 2,4-Cl₂—C₆H₃ | 2,4-Cl₂—C₆H₃ | H | Cl | Cl | H | | |
| 239 | 2,4-Cl₂—C₆H₃ | 2,4-Cl₂—C₆H₃ | Cl | Cl | Cl | H | | |
| 240 | 2,4-Cl₂—C₆H₃ | 4-F—C₆H₄ | H | H | CO₂CH₃ | H | | |
| 241 | 2,4-Cl₂—C₆H₃ | 4-F—C₆H₄ | Br | Cl | CH₃ | H | | |
| 242 | cyclohexyl | C₆H₅ | H | Cl | Cl | H | | |
| 243 | cyclohexyl | C₆H₅ | Cl | H | CN | H | | |
| 244 | cyclohexyl | C₆H₅ | Br | H | H | CH₃ | | |
| 245 | cyclohexyl | 2-Cl—C₆H₄ | H | Cl | Cl | H | | |
| 246 | cyclohexyl | 2-Cl—C₆H₄ | Cl | Cl | Cl | H | | |
| 247 | cyclohexyl | 2-Cl—C₆H₄ | Br | H | CH₃ | H | | |
| 248 | cyclohexyl | 4-Cl—C₆H₄ | H | Cl | Cl | H | | |
| 249 | cyclohexyl | 4-Cl—C₆H₄ | Cl | Cl | Cl | H | | |
| 250 | cyclohexyl | 2,4-Cl₂—C₆H₃ | H | H | CO₂CH₃ | H | | |
| 251 | cyclohexyl | 2,4-Cl₂—C₆H₃ | Cl | H | CO₂CH₃ | H | | |
| 252 | cyclohexyl | 2-F—C₆H₄ | H | H | CH₃ | H | | |
| 253 | cyclohexyl | 2-F—C₆H₄ | Cl | NO₂ | H | H | | |
| 254 | cyclohexyl | 4-F—C₆H₄ | H | Cl | Cl | H | | |
| 255 | cyclohexyl | 4-F—C₆H₄ | Cl | Cl | Cl | H | | |
| 256 | cyclohexyl | 4-F—C₆H₄ | Br | Cl | Cl | H | | |
| 257 | cyclohexyl | 2-Cl-4-F—C₆H₃ | H | H | CO₂CH₃ | H | | |
| 258 | cyclohexyl | 2-Cl-4-F—C₆H₃ | Cl | Cl | Cl | H | | |
| 259 | cyclohexyl | 2-Cl-4-F—C₆H₃ | Br | Cl | CH₃ | H | | |
| 260 | tert.-C₄H₉ | C₆H₅ | H | H | H | CH₃ | | |
| 261 | tert.-C₄H₉ | C₆H₅ | Cl | Cl | Cl | H | | |
| 262 | tert.-C₄H₉ | 2-Cl—C₆H₄ | H | Cl | Cl | H | | |
| 263 | tert.-C₄H₉ | 2-Cl—C₆H₄ | Cl | Cl | CH₃ | H | | |
| 264 | tert.-C₄H₉ | 4-Cl—C₆H₄ | H | Cl | Cl | H | | |
| 265 | tert.-C₄H₉ | 4-Cl—C₆H₄ | H | H | CO₂CH₃ | H | | |
| 266 | tert.-C₄H₉ | 4-Cl—C₆H₄ | H | Cl | CH₃ | H | | |
| 267 | tert.-C₄H₉ | 4-Cl—C₆H₄ | H | H | CH₃ | H | | |
| 268 | tert.-C₄H₉ | 4-Cl—C₆H₄ | H | H | H | CH₃ | | |
| 269 | tert.-C₄H₉ | 4-Cl—C₆H₄ | Cl | Cl | Cl | H | | |

TABLE 1-continued

I

| Ex. | R¹ | R² | E | X | Y | Z | m.p./IR | Isomer |
|---|---|---|---|---|---|---|---|---|
| 270 | tert.-C₄H₉ | 4-Cl—C₆H₄ | Cl | H | CO₂CH₃ | H | | |
| 271 | tert.-C₄H₉ | 4-Cl—C₆H₄ | Cl | Cl | CH₃ | H | | |
| 272 | tert.-C₄H₉ | 4-Cl—C₆H₄ | Cl | H | CH₃ | H | | |
| 273 | tert.-C₄H₉ | 4-Cl—C₆H₄ | Cl | H | H | CH₃ | | |
| 274 | tert.-C₄H₉ | 4-Cl—C₆H₄ | Br | Cl | Cl | H | | |
| 275 | tert.-C₄H₉ | 4-Cl—C₆H₄ | Br | H | CO₂CH₃ | H | | |
| 276 | tert.-C₄H₉ | 4-Cl—C₆H₄ | Br | Cl | CH₃ | H | | |
| 277 | 2,4-Cl₂—C₆H₃ | 2-Cl—C₆H₄ | H | Cl | Cl | H | | |
| 278 | 2,4-Cl₂—C₆H₃ | 2-Cl—C₆H₄ | Cl | H | CO₂CH₃ | H | | |
| 279 | 2,4-Cl₂—C₆H₃ | 4-Cl—C₆H₄ | H | Cl | Cl | H | | |
| 280 | 2,4-Cl₂—C₆H₃ | 4-Cl—C₆H₄ | Cl | Cl | Cl | H | | |
| 281 | 2,4-Cl₂—C₆H₃ | 2,4-Cl₂—C₆H₃ | Cl | Cl | Cl | H | | |
| 282 | 2,4-Cl₂—C₆H₃ | 2,4-Cl₂—C₆H₃ | H | H | CH₃ | H | | |
| 283 | 2,4-Cl₂—C₆H₃ | 4-F—C₆H₄ | H | Cl | CH₃ | H | | |
| 284 | 2,4-Cl₂—C₆H₃ | 2-F—C₆H₄ | H | H | H | CH₃ | | |
| 285 | 4-Br—C₆H₄ | 4-C(CH₃)₃—C₆H₄ | H | H | CH₃ | H | | |
| 286 | 2-OCH₃—C₆H₄ | 2-Cl—C₆H₄ | H | Cl | Cl | H | | |
| 287 | 2-OCH₃—C₆H₄ | 4-Cl—C₆H₄ | Cl | H | CO₂CH₃ | H | | |
| 288 | 2-OCH₃—C₆H₄ | 2-C₁₀H₇ | H | H | Cl | H | | |
| 289 | 2-OCH₃—C₆H₄ | 4-F—C₆H₄ | H | H | CO₂CH₃ | H | | |
| 290 | 2-OCH₃—C₆H₄ | 2-F—C₆H₄ | H | Cl | Cl | H | | |
| 291 | 2-C₁₀H₇ | 2-Cl—C₆H₄ | H | Cl | Cl | H | | |
| 292 | 2-C₁₀H₇ | 4-F—C₆H₄ | Cl | H | Cl | H | | |
| 293 | 4-F—C₆H₄ | 2-Cl—C₆H₄ | H | H | COCH₃ | CH₃ | 130–131° C. | cis |
| 294 | 4-F—C₆H₄ | 2-Cl—C₆H₄ | Cl | H | COCH₃ | CH₃ | | |
| 295 | 4-F—C₆H₄ | 2-Cl—C₆H₄ | Br | H | COCH₃ | CH₃ | | |
| 296 | 4-F—C₆H₄ | 2-CF₃—C₆H₄ | F | Cl | Cl | H | | |
| 297 | 4-F—C₆H₄ | 2-Cl—C₆H₄ | F | Cl | CH₃ | H | | |
| 298 | 4-F—C₆H₄ | 2-Cl—C₆H₄ | F | H | Cl | H | | |
| 299 | 4-F—C₆H₄ | 2-Cl—C₆H₄ | F | H | CN | H | | |
| 300 | 4-F—C₆H₄ | 4-Cl—C₆H₄ | F | Cl | Cl | H | | |
| 301 | 4-F—C₆H₄ | 4-Cl—C₆H₄ | F | Cl | CH₃ | H | | |
| 302 | 4-F—C₆H₄ | 2-Cl-4-F—C₆H₃ | F | Cl | Cl | H | | |
| 303 | 4-F—C₆H₄ | 2-F—C₆H₄ | F | H | CN | H | | |
| 304 | 4-F—C₆H₄ | 4-F—C₆H₄ | F | Cl | CH₃ | H | | |
| 305 | 4-F—C₆H₄ | 2,4-F₂—C₆H₃ | F | Cl | Cl | H | | |
| 306 | 4-F—C₆H₄ | 2,6-F₂—C₆H₃ | F | Cl | Cl | H | | |
| 307 | 4-F—C₆H₄ | 2,4-Cl₂—C₆H₃ | F | H | COCH₃ | CH₃ | | |
| 308 | 4-F—C₆H₄ | 2-OCH₃—C₆H₄ | F | Cl | Cl | H | | |
| 309 | 4-F—C₆H₄ | 4-OCH₃—C₆H₄ | F | H | CN | H | | |
| 310 | 4-F—C₆H₄ | C₆H₅ | F | Cl | CH₃ | H | | |
| 311 | 4-F—C₆H₄ | cyclohexyl | F | Cl | Cl | H | | |
| 312 | C₆H₅ | 4-Cl—C₆H₄ | F | Cl | Cl | H | | |
| 313 | 4-Cl—C₆H₄ | 4-Cl—C₆H₄ | F | Cl | CH₃ | H | | |
| 314 | cyclohexyl | 4-F—C₆H₄ | F | Cl | Cl | H | | |
| 315 | 4-F—C₆H₄ | 2-Cl—C₆H₄ | H | H | COCH₃ | H | resin | cis |
| 316 | 4-F—C₆H₄ | 2-Cl—C₆H₄ | H | COCH₃ | CH₃ | H | 136–141° C. | cis |
| 317 | 4-F—C₆H₄ | 2-Cl—C₆H₄ | H | H | phenyl | H | resin | D1:D2 = 2:1 |
| 318 | 4-F—C₆H₄ | 2-Cl—C₆H₄ | H | H | H | phenyl | | |
| 319 | 4-F—C₆H₄ | C₆H₅ | H | H | CN | H | 126–130° C. | cis |
| 320 | 4-F—C₆H₄ | 2-F-3Cl—C₆H₃ | H | Cl | Cl | H | 150–153° C. | cis |
| 321 | 4-F—C₆H₄ | 4-OCF₃—C₆H₄ | H | H | CO₂CH₃ | H | resin | cis |
| 322 | C₆H₅ | 2-OCH₃—C₆H₄ | H | Cl | Cl | H | resin | cis |
| 323 | 4-F—C₆H₄ | 2-Br—C₆H₄ | H | H | CO₂CH₃ | H | resin | cis |
| 324 | 4-F—C₆H₄ | 2-Cl—C₆H₄ | H | CO₂CH₃ | CO₂CH₃ | H | 134–140° C. | cis |

TABLE 2

| Ex. | R¹ | R² | E | X | Y | Z | m.p./IR | Isomer |
|---|---|---|---|---|---|---|---|---|
| 1a | 4-F—C₆H₄ | 2-Cl—C₆H₄ | H | NO₂ | H | H | 161–165° C. | Z |
| 2a | 4-F—C₆H₄ | 2-Cl—C₆H₄ | H | H | CO₂CH₃ | H | 132–135° C. | Z |
| 3a | 4-F—C₆H₄ | 2-Cl—C₆H₄ | H | Cl | Cl | H | 84–89° C. | Z |

TABLE 2-continued $$\begin{array}{c} Y\diagdown\phantom{xx}X \\ \phantom{x}\diagdown\phantom{x}\diagup \\ N\phantom{xxx}N-E \\ \diagdown\phantom{x}\diagup\phantom{xx}| \\ C\phantom{xxxx}R^1-C=CH-R^2 \\ | \\ Z \end{array}$$

| Ex. | $R^1$ | $R^2$ | E | X | Y | Z | m.p./IR | Isomer |
|---|---|---|---|---|---|---|---|---|
| 4a | 4-F—$C_6H_4$ | 2-Cl—$C_6H_4$ | H | H | CN | H | 99-108° C. | Z/E = 6:1 |
| 5a | 4-F—$C_6H_4$ | 2-Cl—$C_6H_4$ | H | Cl | $CH_3$ | H | resin | Z/E = 3:2 |
| 6a | 4-F—$C_6H_4$ | 2-Cl—$C_6H_4$ | H | H | H | $CH_3$ | 1603, 1509, 1228 846, 830, 759 cm$^{-1}$ | Z |
| 7a | 4-F—$C_6H_4$ | 2-Cl—$C_6H_4$ | H | H | $CH_3$ | H | 93-95° C. | Z |
| 8a | 4-F—$C_6H_4$ | 2-Cl—$C_6H_4$ | Cl | Cl | Cl | H | 1603, 1510, 1470, 1233, 847, 753 cm$^{-1}$ | E |
| 9a | 4-F—$C_6H_4$ | 2-Cl—$C_6H_4$ | Cl | Cl | $CH_3$ | H | | |
| 10a | 4-F—$C_6H_4$ | 2-Cl—$C_6H_4$ | Br | Cl | Cl | H | 172-175° C. | E |
| 11a | 4-F—$C_6H_4$ | 2-Cl—$C_6H_4$ | Br | Cl | $CH_3$ | H | | |
| 12a | 4-F—$C_6H_4$ | 4-Cl—$C_6H_4$ | H | Cl | Cl | H | | |
| 13a | 4-F—$C_6H_4$ | 4-Cl—$C_6H_4$ | Cl | Cl | Cl | H | | |
| 14a | 4-F—$C_6H_4$ | 4-Cl—$C_6H_4$ | Br | Cl | Cl | H | | |
| 15a | 4-F—$C_6H_4$ | 2,4-$Cl_2$—$C_6H_3$ | H | H | $CO_2CH_3$ | H | | |
| 16a | 4-F—$C_6H_4$ | 2,4-$Cl_2$—$C_6H_3$ | Cl | H | $CO_2CH_3$ | H | | |
| 17a | 4-F—$C_6H_4$ | 2,4-$Cl_2$—$C_6H_3$ | Br | H | $CO_2CH_3$ | H | | |
| 18a | 4-F—$C_6H_4$ | 2-Cl-4-F—$C_6H_3$ | H | Cl | Cl | H | | |
| 19a | 4-F—$C_6H_4$ | 2-Cl-4-F—$C_6H_3$ | Cl | Cl | Cl | H | | |
| 20a | 4-F—$C_6H_4$ | 2-Cl-4-F—$C_6H_3$ | Br | Cl | Cl | H | | |
| 21a | 4-F—$C_6H_4$ | 2-$CF_3$—$C_6H_4$ | H | $NO_2$ | H | H | | |
| 22a | 4-F—$C_6H_4$ | 2-$CF_3$—$C_6H_4$ | H | H | $CO_2CH_3$ | H | | |
| 23a | 4-F—$C_6H_4$ | 2-$CF_3$—$C_6H_4$ | H | Cl | Cl | H | 1604, 1561, 1316, 1126, 768 cm$^{-1}$ | E/Z = 2:1 |
| 24a | 4-F—$C_6H_4$ | 2-$CF_3$—$C_6H_4$ | H | H | CN | H | | |
| 25a | 4-F—$C_6H_4$ | 2-$CF_3$—$C_6H_4$ | H | Cl | $CH_3$ | H | 1510, 1316, 1167 1123, 769 cm$^{-1}$ | E/ = 2:1 |
| 26a | 4-F—$C_6H_4$ | 2-$CF_3$—$C_6H_4$ | H | H | H | $CH_3$ | | |
| 27a | 4-F—$C_6H_4$ | 2-$CF_3$—$C_6H_4$ | H | H | $CH_3$ | H | | |
| 28a | 4-F—$C_6H_4$ | 2-$CF_3$—$C_6H_4$ | Cl | Cl | Cl | H | | |
| 29a | 4-F—$C_6H_4$ | 2-$CF_3$—$C_6H_4$ | Cl | H | $CO_2CH_3$ | H | | |
| 30a | 4-F—$C_6H_4$ | 2-$CF_3$—$C_6H_4$ | Cl | Cl | $CH_3$ | H | | |
| 31a | 4-F—$C_6H_4$ | 2-$CF_3$—$C_6H_4$ | Br | Cl | Cl | H | | |
| 32a | 4-F—$C_6H_4$ | 2-$CF_3$—$C_6H_4$ | Br | Cl | $CH_3$ | H | | |
| 33a | 4-F—$C_6H_4$ | 2-$CF_3$—$C_6H_4$ | Br | H | $CO_2CH_3$ | H | | |
| 34a | 4-F—$C_6H_4$ | 4-$CF_3$—$C_6H_4$ | H | Cl | Cl | H | | |
| 35a | 4-F—$C_6H_4$ | 4-$CF_3$—$C_6H_4$ | Cl | H | $CO_2CH_3$ | H | | |
| 36a | 4-F—$C_6H_4$ | 4-$CF_3$—$C_6H_4$ | Br | Cl | $CH_3$ | H | | |
| 37a | 4-F—$C_6H_4$ | 2-F—$C_6H_4$ | H | Cl | Cl | H | | |
| 38a | 4-F—$C_6H_4$ | 2-F—$C_6H_4$ | H | Cl | $CH_3$ | H | | |
| 39a | 4-F—$C_6H_4$ | 2-F—$C_6H_4$ | Cl | Cl | Cl | H | | |
| 40a | 4-F—$C_6H_4$ | 2-F—$C_6H_4$ | Cl | H | $CO_2CH_3$ | H | | |
| 41a | 4-F—$C_6H_4$ | 2-F—$C_6H_4$ | Br | Cl | Cl | H | | |
| 42a | 4-F—$C_6H_4$ | 2-F—$C_6H_4$ | Br | Cl | $CH_3$ | H | | |
| 43a | 4-F—$C_6H_4$ | 4-F—$C_6H_4$ | H | Cl | Cl | H | | |
| 44a | 4-F—$C_6H_4$ | 4-F—$C_6H_4$ | H | H | $CO_2CH_3$ | H | | |
| 45a | 4-F—$C_6H_4$ | 4-F—$C_6H_4$ | Cl | Cl | Cl | H | | |
| 46a | 4-F—$C_6H_4$ | 4-F—$C_6H_4$ | Cl | H | $CO_2CH_3$ | H | | |
| 47a | 4-F—$C_6H_4$ | 4-F—$C_6H_4$ | Br | Cl | Cl | H | | |
| 48a | 4-F—$C_6H_4$ | 4-Cl—$C_6H_4$ | Br | H | $CO_2CH_3$ | H | | |
| 49a | 4-F—$C_6H_4$ | 2,4-$F_2$—$C_6H_3$ | H | Cl | Cl | H | | |
| 50a | 4-F—$C_6H_4$ | 2,4-$F_2$—$C_6H_3$ | H | H | $CO_2CH_3$ | H | | |
| 51a | 4-F—$C_6H_4$ | 2,4-$F_2$—$C_6H_3$ | Cl | Cl | Cl | H | | |
| 52a | 4-F—$C_6H_4$ | 2,4-$F_2$—$C_6H_3$ | Cl | H | $CO_2CH_3$ | H | | |
| 53a | 4-F—$C_6H_4$ | 2,4-$F_2$—$C_6H_3$ | Br | Cl | Cl | H | | |
| 54a | 4-F—$C_6H_4$ | 2,4-$F_2$—$C_6H_3$ | Br | H | $CO_2CH_3$ | H | | |
| 55a | 4-F—$C_6H_4$ | 2,6-$F_2$—$C_6H_3$ | H | Cl | Cl | H | | |
| 56a | 4-F—$C_6H_4$ | 2,6-$F_2$—$C_6H_3$ | H | H | $CO_2CH_3$ | H | | |
| 57a | 4-F—$C_6H_4$ | 2,6-$F_2$—$C_6H_3$ | Cl | Cl | Cl | H | | |
| 58a | 4-F—$C_6H_4$ | 2,6-$F_2$—$C_6H_3$ | Cl | H | $CO_2CH_3$ | H | | |
| 59a | 4-F—$C_6H_4$ | 2,6-$F_2$—$C_6H_3$ | Br | Cl | Cl | H | | |
| 60a | 4-F—$C_6H_4$ | 2,6-$F_2$—$C_6H_3$ | Br | H | $CO_2CH_3$ | H | | |
| 61a | 4-F—$C_6H_4$ | 2-$OCH_3$—$C_6H_4$ | H | Cl | Cl | H | resin | E/Z = 3:1 |
| 62a | 4-F—$C_6H_4$ | 2-$OCH_3$—$C_6H_4$ | H | Cl | $CH_3$ | H | 1599, 1509, 1248, 1225, 754 cm$^{-1}$ | E/Z = 3:1 |
| 63a | 4-F—$C_6H_4$ | 2-$OCH_3$—$C_6H_4$ | H | H | CN | H | resin | E/Z = 3:1 |
| 64a | 4-F—$C_6H_4$ | 2-$OCH_3$—$C_6H_4$ | H | H | $CH_3$ | H | 1599, 1509, 1247, 754 cm$^{-1}$ | E/Z = 3:1 |
| 65a | 4-F—$C_6H_4$ | 2-$OCH_3$—$C_6H_4$ | H | H | $CO_2CH_3$ | H | 1720, 1509, 1248, 1116, 755 cm$^{-1}$ | E/Z = 3:1 |
| 66a | 4-F—$C_6H_4$ | 2-$OCH_3$—$C_6H_4$ | Cl | Cl | Cl | H | | |
| 67a | 4-F—$C_6H_4$ | 2-$OCH_3$—$C_6H_4$ | Br | H | $CO_2CH_3$ | H | | |

TABLE 2-continued

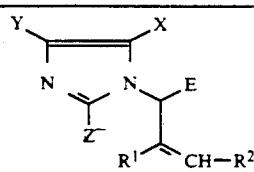

| Ex. | R¹ | R² | E | X | Y | Z | m.p./IR | Isomer |
|---|---|---|---|---|---|---|---|---|
| 68a | 4-F—C₆H₄ | 4-OCF₃—C₆H₄ | H | Cl | Cl | H | | |
| 69a | 4-F—C₆H₄ | 4-OCF₃—C₆H₄ | Cl | Cl | Cl | H | | |
| 70a | 4-F—C₆H₄ | 4-OCF₃—C₆H₄ | Br | Cl | Cl | H | | |
| 71a | 4-F—C₆H₄ | C₆H₅ | H | Cl | Cl | H | | |
| 72a | 4-F—C₆H₄ | C₆H₅ | Cl | H | CO₂CH₃ | H | | |
| 73a | 4-F—C₆H₄ | cyclohexyl | H | Cl | Cl | H | | |
| 74a | 4-F—C₆H₄ | cyclohexyl | Cl | H | CH₃ | H | | |
| 75a | C₆H₅ | C₆H₅ | H | Cl | Cl | H | | |
| 76a | C₆H₅ | C₆H₅ | Cl | H | H | CH₃ | | |
| 77a | C₆H₅ | C₆H₅ | Br | H | CO₂CH₃ | H | | |
| 78a | C₆H₅ | 4-Cl—C₆H₄ | H | Cl | Cl | H | | |
| 79a | C₆H₅ | 2-Cl—C₆H₄ | Cl | Cl | Cl | H | | |
| 80a | C₆H₅ | 2,4-Cl₂—C₆H₃ | Br | H | CO₂CH₃ | H | | |
| 81a | C₆H₅ | 4-F—C₆H₄ | H | Cl | Cl | H | | |
| 82a | C₆H₅ | 2-F—C₆H₄ | H | Cl | Cl | H | | |
| 83a | 4-Cl—C₆H₄ | C₆H₅ | H | Cl | Cl | H | | |
| 84a | 4-Cl—C₆H₄ | 2-Cl—C₆H₄ | H | Cl | Cl | H | | |
| 85a | 4-Cl—C₆H₄ | 2-Cl—C₆H₄ | Cl | Cl | Cl | H | | |
| 86a | 4-Cl—C₆H₄ | 2,4-Cl₂—C₆H₃ | Br | H | CH₃ | H | | |
| 87a | 4-Cl—C₆H₄ | 4-F—C₆H₄ | H | Cl | Cl | H | | |
| 88a | 4-Cl—C₆H₄ | 2-F—C₆H₄ | H | Cl | Cl | H | | |
| 89a | 2-Cl—C₆H₄ | 2-Cl—C₆H₄ | H | Cl | Cl | H | | |
| 90a | 2-Cl—C₆H₄ | 2-F—C₆H₄ | H | Cl | Cl | H | | |
| 91a | 2-F—C₆H₄ | 2-F—C₆H₄ | H | Cl | Cl | H | | |
| 92a | 2-F—C₆H₄ | 2-F—C₆H₄ | H | Cl | Cl | H | | |
| 93a | 2-F—C₆H₄ | 4-F—C₆H₄ | Br | Cl | Cl | H | | |
| 94a | 2-F—C₆H₄ | 4-F—C₆H₄ | H | Cl | Cl | H | | |
| 95a | cyclohexyl | 2-Cl—C₆H₄ | H | Cl | Cl | H | | |
| 96a | cyclohexyl | 4-Cl—C₆H₄ | Cl | Cl | Cl | H | | |
| 97a | cyclohexyl | 4-F—C₆H₄ | H | Cl | Cl | H | | |
| 98a | 4-F—C₆H₄ | 2-Cl—C₆H₄ | F | CH₃ | Cl | H | | |
| 99a | 4-F—C₆H₄ | 2-Cl—C₆H₄ | F | Cl | Cl | H | | |
| 100a | 4-F—C₆H₄ | 4-Cl—C₆H₄ | F | H | CN | H | | |
| 101a | 4-F—C₆H₄ | 2,4-Cl₂—C₆H₃ | F | H | CN | H | | |
| 102a | 4-F—C₆H₄ | 2-Cl-4-F—C₆H₃ | F | Cl | Cl | H | | |
| 103a | 4-F—C₆H₄ | 2-CF₃—C₆H₄ | F | CH₃ | Cl | H | | |
| 104a | 4-F—C₆H₄ | 4-CF₃—C₆H₄ | F | Cl | Cl | H | | |
| 105a | 4-F—C₆H₄ | 2-F—C₆H₄ | F | H | CH₃ | H | | |
| 106a | 4-F—C₆H₄ | 4-F—C₆H₄ | F | Cl | Cl | H | | |
| 107a | 4-F—C₆H₄ | 2,4-F₂—C₆H₃ | F | H | CO₂CH₃ | H | | |
| 108a | 4-F—C₆H₄ | 2-OCH₃—C₆H₃ | F | H | CO₂CH₃ | H | | |
| 109a | 4-F—C₆H₄ | 4-OCF₃—C₆H₄ | F | Cl | Cl | H | | |
| 110a | C₆H₅ | 4-Cl—C₆H₄ | F | Cl | Cl | H | | |

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
Erysiphe graminin in cereals,
Perysiphe cichoracearum and Sphaerotheca fuliginea in cucurbits,
Podosphaera leucotricha in apples,
Uncinula necator in vines,
Puccinia species in cereals,
Rhizoctonia species in cotton and lawns,
Ustilago species in cereals and sugar cane,
Venturia inaequalis (scab) in apples,
Helminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Verticillium species in various plants,
Plasmopara viticola in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, for example against *Paecilomyces variotii.*

The agents and the ready-to-use formulations prepared from them such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 113 is mixed with 10 parts by weight of N-methyl-α-pyrrolidone. A mixture is obtained which is suitable for application in the form of very fine drops.

II. 20 parts by weight of compound no. 115 is dissolved in a mixture consisting of 80 parts by weight of xylene, 10 parts by weight of the adduct of 8 to 10 moles of ethylene oxide and 1 mole of oleic acid-N-monethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no 113 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no 115 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 113 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 115 is intimately mixed with 97 parts by weight of particulate kaolin. A dust is obtained containing 3% by weight of the active ingredient.

VII. 30 parts by weight of compound no. 113 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 115 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 113 is intimately mixed with 2 parts by weight of the calcium salt of dodecylbenzenesulfonic acid, 8 parts by weight of a fatty alcohol polyglycol ethr, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

The following list of fungicides with which the novel compounds may be combined is intended to illustrate possible combinations but not to impose any restrictions.

Examples of fungicides which may be combined with the novel compounds are;

sulfur, dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;

nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;

heterocyclic substances, such as
2-heptadecylimidazol-2-yl acetate,
2,4-dichloro-6-(o-chloroanilino)-s-triazine,
O,O-diethyl phthalimidophosphonothiote,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate, 2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-carboxanilido-6-methyl-1,4-oxathiyne,
2,3-dihydro-carboxanilido-6-methyl-1,4-oxathiyne 4,4-dioxide,
2-methylfuran-3-carboxanilide,
3 2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alenate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-[3,5-dichlorophenyl]-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,3-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

Use example

For comparison purposes, cis-2-(imidazol-1-ylmethyl)-2-(4-fluorophenyl)-3-(2,6-difluorophenyl)-oxirane (A) disclosed in DE 3,218,130 was used.

Use example

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of *Plasmopara viticola*. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results show that active ingredients 113 and 115, applied as 0.05 wt % spray liquors, had a better fungicidal action (95%) than prior art comparative agent A (60%).

We claim:

1. Substituted imidazolylmethyloxiranes and substituted imidazolylpropenes of the general formula I

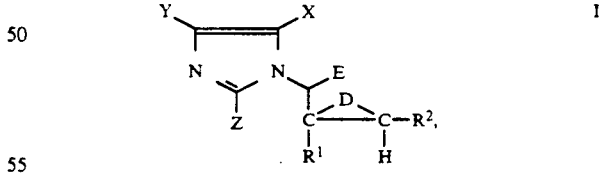

where
R$^1$ and R$^2$ are identical or different and each is C$_1$-C$_8$-alkyl, C$_3$-C$_8$-cycloalkyl, C$_5$-C$_8$-cycloalkenyl, tetrahydropyranyl, norbornyl, pyridyl, naphthyl, biphenyl or phenyl, each of which is unsubstituted or mono- to trisubstituted by halogen, nitro, phenoxy, amino, alkyl, alkoxy or haloalkyl, each of 1 to 4 carbon atoms,
D is oxygen or a single bond,
E is H, F, Cl or Br,
X, Y and Z are identical or different and each is hydrogen or C$_1$-C$_3$-alkyl, X, Y and Z not simultaneously being hydrogen, and acid addition salts and metal complexes thereof tolerated by plants.

2. Substituted imidazolylmethyloxiranes and substituted imidazolylpropenes of the general formula I, where $R^1$ and $R^2$ are phenyl which is unsubstituted or mono- or disubstituted by fluorine, chlorine, bromine or trifluoromethyl.

3. A fungicidal composition comprising a carrier and a fungicidally effective amount of an imidazolylmethyloxirane or an imidazolylpropene of the formula I

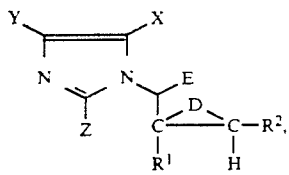

where
$R^1$ and $R^2$ are identical or different and each is $C_1$–$C_8$-alkyl, $C_3$–$C_8$-cycloalkyl, $C_5$–$C_8$-cycloalkenyl, tetrahydropyranyl, norbornyl, pyridyl, naphthyl, biphenyl or phenyl, each of which is unsubstituted or mono- to trisubstituted by halogen, nitro, phenoxy, amino, alkyl, alkoxy or haloalkyl, each of 1 to 4 carbon atoms,
D is oxygen or a single bond,
E is H, F, Cl or Br,
X, Y and Z are identical or different and each is hydrogen or $C_1$–$C_3$-alkyl, X, Y and Z not simultaneously being hydrogen, and acid addition salt or metal complex thereof tolerated by plants.

4. A process for combating fungi, wherein a fungicidally effective amount of a substituted imidazolylmethyloxirane or of a substituted imidazolylpropene of the formula I

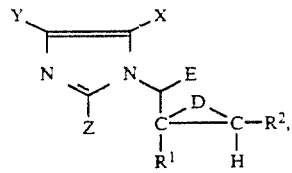

where
$R^1$ and $R^2$ are identical or different and each is $C_1$–$C_8$-alkyl, $C_3$–$C_8$-cycloalkyl, $C_5$–$C_8$-cycloalkenyl, tetrahydropyranyl, norbornyl, pyridyl, naphthyl, biphenyl or phenyl, each of which is unsubstituted or mono- to trisubstituted by halogen, nitro, phenoxy, amino, alkyl, alkoxy or haloalkyl, each of 1 to 4 carbon atoms,
D is oxygen or a single bond,
E is H, F, Cl or Br,
X, Y and Z are identical or different and each is hydrogen or $C_1$–$C_3$-alkyl, X, Y and Z not simultaneously being hydrogen, or an acid addition salt or metal complex thereof tolerated by plants, is allowed to act on the fungi or the materials, areas, plants or seed threatened by fungus attack.

* * * * *